United States Patent [19]
Grant et al.

[11] Patent Number: 5,888,553
[45] Date of Patent: Mar. 30, 1999

[54] NON-STEROIDAL ANABOLIC COMPOSITION

[75] Inventors: Douglas D. Grant; Stanley A Bynum, both of Mesa, Ariz.; H. DeWayne Ashmead, Fruit Heights, Utah

[73] Assignees: Infinity, Inc., Mesa, Ariz.; Albion International, Inc., Clearfield, Utah

[21] Appl. No.: 826,926

[22] Filed: Apr. 8, 1997

[51] Int. Cl.$^6$ .......................... A01N 59/16; A01N 57/10; A01N 55/02; A61K 38/16
[52] U.S. Cl. .............................. 424/655; 514/6; 514/184; 514/505
[58] Field of Search ................................... 424/655, 677; 514/6, 18, 561, 184, 505; 435/18

[56] References Cited

U.S. PATENT DOCUMENTS

| | | | |
|---|---|---|---|
| 4,020,158 | 4/1977 | Ashmead et al. | 424/177 |
| 4,076,803 | 2/1978 | Ashmead | 424/177 |
| 4,167,564 | 9/1979 | Jensen | 424/177 |
| 4,599,152 | 7/1986 | Ashmead | 204/72 |
| 4,774,089 | 9/1988 | Ashmead | 424/157 |
| 4,830,716 | 5/1989 | Ashmead | 204/72 |
| 4,863,898 | 9/1989 | Ashmead et al. | 514/6 |
| 4,954,492 | 9/1990 | Jensen | 514/188 |

OTHER PUBLICATIONS

Sartin et al. *Plasma Concentrations of Metabolic Hormones in High and Low Producing Dairy Cows*, 71 J. Dairy Sci. 650–657, 1988.

Schrauzer, et al. *Effects of Chromium Supplementation on Food Energy Utilization and the Trace–Element Composition in the Liver and Heart of Glucose–Exposed Young Mice*, 9 Biol. Trace Element Res. 79, 1986.

Polansky, et al. *Beneficial Effects of Supplemental Chromium (Cr) on Glucose, Insulin and Glucagon of Subjects Consuming Controlled Low Chromium Diets*, FASEB J. A2964, 1990.

Satterlee et al. *Vitamin C Amelioration of the Adrenal Stress Response in Broiler Chickens being Prepared for Slaughter*, 94A Comp. Biochem. Physiol. 569–574, 1989.

Munck et al. *Physiological Functions of Glucocorticoids in Stress and Their Relation to Pharmacological Actions*, 5 Endoc. Rev. 25, 1984.

Southorn et al. *The Effect of Corticosterone Treatment of the Response of Muscle Protein Synthesis to Insulin Infusion in the Rat*, 23 J. Endocrin. Abst. #127, 1989.

Rennie et al. *Glutamine Transport and Its Metabolic Effects*, 124 J. Nutri. 1503S–1508S, 1994.

Gore et al. *Glutamine Kinetics in Burn Patients*, 129 Arch. Surg. 1318–1323, 1994.

Young et al. *Patients Receiving Glutamine–Supplemented Intravenous Feedings Report an Improvement in Mood*, 17 J. Parenteral and Enteral Nutrition, 422–427, 1993.

*Primary Examiner*—Jose' G. Dees
*Assistant Examiner*—Alton Pryor
*Attorney, Agent, or Firm*—Thorpe, North & Western

[57] ABSTRACT

A non-steroid containing anabolic nutrient formulation for the building and sustaining of muscle mass in humans or other warm-blooded animals, that enables the body to synthesize and maintain muscle at a mass and in a manner optimally suited to the genetic makeup of that person or animal. The formulation comprises effective amounts of a chromium salt, complex or chelate and a magnesium glycyl glutaminate chelate. Optionally, one or more additional nutrients selected from the group consisting of a magnesium amino acid chelate or proteinate, an α-glutaric acid salt of ornithine, creatine or a salt thereof, and a branched chain amino acid selected from the group consisting of leucine, isoleucine and valine and mixtures thereof may be included.

38 Claims, No Drawings

NON-STEROIDAL ANABOLIC COMPOSITION

FIELD OF THE INVENTION

The present invention relates generally to nutrient compositions that sustain and promote muscle mass, and more particularly to anabolic compositions comprising proteins and a blend of nutrients comprising, at a minimum, a magnesium glycyl glutaminate chelate and a chromium salt, complex or chelate.

BACKGROUND OF THE INVENTION

It is well known that both negative energy balance and muscle catabolism are consequences of physiological stress that often accompanies protein calorie malnutrition, strenuous physical exercise, physical trauma, burn injury, surgical trauma, malnutrition, maldigestion, malabsorption, hyperthyroidism, chemotherapy, radiation therapy, anorexia, cachexia, short bowel syndrome, old age, sepsis and other conditions. It is also known that maintaining a positive metabolic energy balance can help to alleviate such problems and also has a sparing effect on muscle catabolism that occurs during strenuous physical exertion causing fatigue.

Athletes, in particular, have needs for maintaining and/or building muscle mass compatible with their genetic makeup to optimize their strength, body tone and physical abilities. Ideally, this would be accomplished using the body's own resources without being subjected to the administration of anabolic steroids and the associated negative side effects.

It is well known that anabolic steroids, such as testosterone and natural and synthetic derivatives and substitutes, affect many metabolic activities such as muscular development and fat distribution. Administration of anabolic steroids tend to take users past their natural or genetic limits to create body size and muscle mass beyond that which is optimal to the genetic makeup of the individual and past that which can be effectively supported by the various organs of the body.

Excess anabolic steroids tend to suppress or dam up other natural, yet essential, hormones in the body such as the andrenocorticosteroids. The glucocorticoids, and cortisol (hydrocortisone) in particular, are necessary in the metabolism of carbohydrates and fats. Cortisol promotes gluconeogenesis by peripheral and hepatic actions. It acts to mobilize proteins and amino acids from skeletal muscle. Proteins and amino acids funnel into the liver, where they engage the enzyme systems involved in the production of glucose and glycogen. In quantitative terms, the peripheral action of cortisol accounts in large measure for its gluconeogenic effect. In the liver, especially on a long term basis, cortisol induces the synthesis of a number of enzymes intimately involved in gluconeogenesis.

However, release or administration of large doses of cortisol can produce changes in carbohydrate, protein and fat metabolism. Blood sugar tends to be high, liver glycogen is increased and there is increased resistance to insulin. The catabolic action of cortisol is reflected in the wasting of tissues, reduced mass of muscle, osteoporosis and thinning of the skin. In certain instances, a diabetic-like state may be produced.

Excess amounts of cortisol also causes an alteration in fat distribution. There is a gain of fat in depots in the neck, supraclavicular area and cheeks and a loss of fat from the extremities.

Elevated cortisol levels are also known to suppress the immune system. Cortisol prevents glucose entry into muscle and adipose tissue and decreases activity of insulin. Moreover, cortisol has been shown to inhibit LH release in the bovine species and therefore has an effect on reproduction. Insulin availability may limit the onset of ovarian activity in the female leading to ovulation. Insulin is also known to reduce concentration of blood ketone bodies. Sartin et al., *Plasma Concentrations of Metabolic Hormones in High and Low Producing Dairy Cows*, J. Dairy. Sci. 71:650–657, 1988 reports that cortisol is antagonistic to milk production.

Chromium has been shown to suppress the production of glucocorticoids. Chromium functions as a potentiator of insulin. Chromium is a trivalent mineral which has been found in recent years to be more bioavailable when administered as an organic complex. The most common organic complex is a low-molecular weight organic complex termed "glucose tolerance factor" (GTF) obtained primarily from Brewer's yeast. Recent research has shown that various stressors such as infection, strenuous exercise, pregnancy, change of environment, etc, increase urinary excretion of chromium. Sub-optimal levels of chromium may be a factor in several stress related diseases. Schnauzer et al., *Effects of Chromium Supplementation in Food Energy Utilization and the Trace-element Composition in the Liver and Heart of Glucose-exposed Young Mice*, Biol. Trace Element Res. 9:79 1986, have shown that chromium supplementation protects against stress-induced losses of trace minerals such as zinc, copper, iron and manganese. Polansky et al., *Beneficial Effects of Supplemental Chromium on Glucose, Insulin and Glucagon of Subjects Consuming Controlled Low Chromium Diets*, FASEB J. A2964. 1990, report that human dietary chromium intakes is suboptimal with diets of approximately twenty-five percent of the U.S. population containing forty percent or less of the recommended daily chromium intake. There is also evidence that chromium in the human body decreases with age. In the animal kingdom, it has been found that steers, subjected to conditions of stress, have increased serum cortisol levels which can be lowered by administration of supplemental chromium.

Moreover, chromium is an essential trace element as a cofactor in several enzyme systems. As mentioned above, it is associated with a low-molecular weight organic complex termed "glucose tolerance factor" (GTF) that acts with insulin in promoting normal glucose utilization. Brewer's yeast, which is rich in GTF, has been shown to improve glucose tolerance, lower serum cholesterol and triglycerides in some subjects and to reduce insulin requirements in some diabetics. Glucose tolerance is usually impaired in protein-calorie malnutrition and some cases have shown a dramatic response to administration of trivalent chromium. Deficiency has been reported in patients on prolonged parenteral feeding. Additionally, GTF is not only a co-factor of insulin thus influencing glucose, but protein and lipid metabolism as well. GTF is not as effective, if not ineffective, in the absence of insulin. The exact mechanism by which GTF improves glucose tolerance is not known. However, it is thought that GTF enhances the binding of insulin to its specific receptors.

Another part of the beneficial effects of chromium on the immune system may be related to vitamin C metabolism. It is known that cattle arriving at a feedlot in a chronically stressed condition show evidence of hyperglycemia and are at greater risk of disease as vitamin C entry into neutrophils is most likely reduced. Vitamin C is needed for neutrophil function, decreases circulating corticoid levels and ameliorates immunosuppression in stress. Nockels, *Effect of Stress on Mineral Requirements*, Western Nutritional Conference, 1990 and Satterlee et al., *Vitamin C Amelioration of the Adrenal Stress Response in Broiler Chickens Being Prepared for Slaughter*, Comp. Biochem. Physiol., 94A:569–574, 1989 have shown that vitamin C ameliorates the negative effect of stress in broiler chickens being prepared for slaughter which is possibly due to suppression of adrenocortical steroidogenesis. Synthesis of ascorbate from glucose may be reduced when glucose is deficient as in earlier fasting during transport. Calves may also have a low glucose synthesis when fed forage diets so vitamin C synthesis may be low.

Glucocorticoids are known to suppress the immune system according to Munck et al, *Physiological Functions of Glucocorticoids in Stress and Their Relation to Pharmacological Actions*, Endoc. Rev. 5:25, 1984. Therefore, another beneficial effect of chromium supplementation during periods of stress in suppressing cortisol serum levels could conceivably result in improving effectiveness of certain vaccines. Carlson et al., *The Bovine Proceedings*, 15:84 1990, measured antibody response to IBR vaccination in feedlot cattle found cattle to be poorly responsive to immunization upon arrival in the feedlot. These results were attributed to the stresses of shipping and respiratory infection drawing the conclusion that such factors may render an animal immunoincompetent.

Supplemental chromium, administered to bovine species, has been shown to decrease serum cortisol and may increase milk production. Supplemental chromium has also has been found to be associated with weight gain in stressed animals. Part of the improvement in gain with administering supplemental chromium may be due to decreasing cortisol production. It has been shown by Southorn et al., *The Effect of Corticosterone Treatment of the Response of Muscle Protein Synthesis to Insulin Infusion in the Rat*, J. Endocrin. 23: abst. #127, 1989, that rats treated with corticosterone developed insulin resistance with respect to muscle protein synthesis. Clinical evidence supports the immunosuppressive activity of glucocorticoids through impairment of neutrophil function and suppression of lymphocyte blastogenesis.

However, once chromium is mobilized in the body in response to increased glucose metabolism, elevated insulin response, stress, elevated cortisol levels, etc., it is not reabsorbed in the tissues but is excreted in the urine. Therefore, diets and/or conditions that lead to chromium utilization also lead to chromium depletion. Sufficient chromium supplementation, in a bioavailable form, is therefore essential to the proper functioning of the metabolic system.

Magnesium is the fourth most abundant cation in the body. Almost half of the magnesium in the body is located in the bone. Of the non-osseous tissues, liver and striated muscle have the highest magnesium concentrations. Magnesium is an activator of a host of enzyme systems that are critical to cellular metabolism. Prominent among these are the enzymes that hydrolyze and transfer the phosphate groups, e.g. the phosphatases and those concerned in the reactions involving adenosine triphosphate (ATP). Since ATP is required for glucose utilization, fat, protein, nucleic acid and coenzyme synthesis, muscle contraction, methyl group transfer, sulfate, acetate and formate activation, by inference the activating effect of magnesium extends to all these functions. One means by which magnesium is involved in protein synthesis is by contributing to the binding of messenger RNA to the 70S ribosome. Magnesium is also required for the synthesis and degradation of DNA and has also been included in all the amino acid activating systems.

By means of one or more of the above mechanisms, magnesium is essential to the building of maximum muscle mass and endurance. Strenuous physical activity and associated mental and physical stress can cause a decline in tissue magnesium levels as a result of hypermetabolic compensation and the increased elaboration of catecholamines, glucagon, and mineral corticoids. Magnesium administered in the form of inorganic salts to replenish reduced levels in the body, can cause serious side effects such as intestinal irritability, loose stools, or diarrhea. Because of this, many body builders or other athletes are magnesium deficient and sufficient levels of magnesium are not included in many prior art anabolic formulas. It is therefore essential that any magnesium administered is in a safe but effective bioavailable form. One such form which has been shown to be superior to all others is as an amino acid chelate.

There are certain amino acids that affect the positive balance of nitrogen in the building or synthesis of skeletal or muscular proteins. These function in the presence or absence of insulin but have a greater response in the presence of insulin. Glutamine, glycine and arginine are all anabolic and also all have well-defined metabolic behaviors that are distinct from their participation in protein synthesis and breakdown. According to Rennie et al., J Nutr. 124: 1503S–1508S (1994) it has been found that there is a strong relationship between the rate of muscle protein synthesis and intramuscular glutamine concentration. Rennie et al. state that there is little doubt that the phenomenon of an anabolic effect of glutamine in human and animal muscle exists, however, the nature of the mechanism is not evident. Glutamine or L-glutamine, not only has a positive effect on the nitrogen balance in protein, i.e. is anabolic, but also stimulates the accumulation of muscle glycogen in rats. It is suggested that any processes that interfere with the ability of muscle to accumulate glutamine will result in muscle wasting and therefore, the effects of disease and injury causing muscle wasting may include interference with the muscle glutamine transporter.

Young et al, J. Parenteral and Enteral Nutrition, 17: 422–427 (1993) states that glutamine has been shown to be clinically safe when administered as a supplemental nutrient and improves nitrogen balance. It is also known that glutamine is a precursor of the neurotransmitter τ-aminobutyric acid and can cross the blood-brain barrier. Glutamate, which is a product of glutamine metabolism, and vice versa, is the most abundant single amino acid within the central nervous system and also functions as a neurotransmitter. Because of this property, Young et al., have found that glutamine also possesses antidepressive properties.

According to Gore, et al., Arch. Surg. 129:1318–1323 (1994) catabolic hormones, such as cortisol, increases the efflux of glutamine resulting from an accelerated release of glutamine from the free intracellular glutamine pool that is then replenished from either increased endogenous protein breakdown or from de novo glutamine synthesis. This is further indication that increased cortisol has an adverse or catabolic affect on the nitrogen balance of muscle tissues and also of the need for a source of bioavailable glutamine.

To permit optimal muscle growth and maintenance, it is essential that a proper balance be maintained between endogenous anabolic steroids and cortisol such that these hormones are present in amounts sufficient to enable the various body processes to function normally while, at the same time, minimizing the adverse side effects caused by these same hormones. It is also necessary that adequate amounts of chromium and magnesium, in a bioavailable form, are present to regulate enzyme functions, cortisol levels, and optimize synthesis of proteins, glucose, and fat distribution.

Ashmead et al., U.S. Pat. No. 4,020,158; Ashmead, U.S. Pat. No. 4,076,803; Jensen U.S. Pat. No. 4,167,564; Ashmead, U.S. Pat. No. 4,774,089 and Ashmead, U.S. Pat. No. 4,863,898 all disclose metal amino acid chelates and various uses for these chelates in reference to increasing absorption of essential minerals into biological tissues. Some of these patents suggest that certain mineral and ligand combinations can enhance metal uptake in specific organs or tissues where specific biological functions are enhanced, i.e. minerals crossing the placental membranes into foeti, estrus or spermatogenesis, etc.

However, although amino acid chelates and some of the uses to which they are applicable are documented in the art, there is no teaching or suggestion that proper formulations and administration of a chromium salt, complex or chelate, in combination with a specific magnesium amino acid chelate (magnesium glycyl glutaminate) can have an anabolic effect in the building and maintaining of muscle mass in a manner which equals or is superior to the administration of anabolic steroids but without having the negative side effect.

It would be desirable to enable the building of muscle mass and strength in a manner consistent with the genetic makeup of an individual without resorting to the use of substances, natural or synthetic, which have a negative physiological impact. It would also be desirable to optimize such building of muscle mass using nutritional supplements which awaken the inherent processes of the body to function at peak natural performance for that particular individual.

OBJECTS AND BRIEF SUMMARY OF THE INVENTION

It is an object of the present invention to provide an anabolic nutrient formulation for the building and sustaining of muscle mass in humans or other warm-blooded animal, which enables the body to synthesize and maintain muscle at a mass and in a manner optimally suited to the genetic makeup of that person or animal.

Another object of this invention is to provide a nutrient formulation which provides anabolic nutrients at a cellular level to promote maximum muscle growth, size and balance consistent with the natural genetic processes and systems of the body.

A further object of this invention is to provide a nutrient formulation which contains, at a minimum, the nutrients chromium, magnesium and glutamine in a bioavailable form and in amounts sufficient to elicit an anabolic response in the body to promote the growth of muscle mass that can be effectively supported by the organs of the body.

Still another object is to provide a method of optimizing mass muscle development and maintain the muscle at amounts which can be supported by the natural genetic makeup of an individual while maintaining reduced but sufficient cortisol levels balanced with endogenous anabolic steroids.

These and other objects may be accomplished by a composition for enteral or parenteral administration comprising effective amounts of a chromium salt, complex or chelate and a magnesium glycyl glutaminate and, optionally, one or more additional nutrients selected from the group consisting of a magnesium amino acid chelate or proteinate, an α-glutaric acid salt of ornithine, creatine or a salt thereof, and a branched chain amino acid selected from the group consisting of leucine, isoleucine and valine and mixtures thereof.

The composition can be administered in any suitable form for oral or enteral administration, i.e. as a tablet, capsule, syrup, elixir, powder or the like. Preferably, the composition will be admixed with a carrier and particularly a protein based carrier which also preferably contains one or more proteolytic enzymes such as a protease, peptidase or acid-stable protease. As such, it can be formulated with flavoring agents and administered as a drink or admixed with solid food. When formulated for parenteral administration it will preferably be as an injectable solution suitable for either intramuscular or intravenous administration.

When administered to individuals actively engaged in exercise and/or strength programs, the composition proved useful in promoting optimal growth and maintenance of muscle mass while, at the same time, reducing cortisol levels.

DETAILED DESCRIPTION OF THE INVENTION

For purposes of this invention the following definitions shall be applicable.

According to definition 57.142 of the AAFCO (American Association of Feed Control Officials) an Amino Acid Chelate (AAC) is as follows:

57.142 Metal Amino (Acid) Chelate is the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800.

"Amino Acid Chelates" for purposes of the present invention are as contained in the above AAFCO definition with the proviso that the molecular weight of the chelates can be as high as 1500 but are preferably not more than 1000 and are most preferably no greater than 800. Such amino acid chelates will have a stability constant of between about $10^6$ and $10^{16}$. Furthermore, more pure forms of amino acid chelates formed by the reaction of amino acids with metal oxides, hydroxides, carbonates, and elemental metals as described in U.S. Pat. No. 4,830,716 and U.S. Pat. No. 4,599,152 and which avoid the presence of unwanted metal salt anions and having the same metal to amino acid mole ratios and molecular weights as described above are also included in this definition. Such more pure forms are actually the preferable forms of amino acid chelates utilized because of the lack of metal salt anions such as chlorides and sulfates.

"Metal proteinate" shall mean the product resulting from the chelation or complexing of a soluble salt with amino acids and/or partially hydrolyzed protein. A metal proteinate is more broadly defined than an amino acid chelate and has no particular molecular weight limitation nor metal to ligand mole ratio. In the formation of a metal proteinate a complete chelate ring may or may not be formed.

"Amino acid complex" shall mean the product resulting from the complexing of an alkali metal, such as sodium or potassium, with an amino acid and/or partially hydrolyzed protein. A monovalent metal, such as sodium or potassium, does not form a cyclic chelate ring and there is only a single bonding site between the amino acid and metal ion. "Amino acid complex" shall also mean the product resulting from the complexing of a metal ion that has a valency of two or more with an amino acid and/or partially hydrolyzed protein. In complex formation only one bond or point of attachment occurs between the ligand and the metal ion and hence a cyclic structure is not formed.

"Magnesium glycyl glutaminate" shall mean an amino acid chelate formed using the amino acids glycine and glutamine as the ligands. Preferably one mole of each amino acid will form coordinate covalent bonds with the magnesium ion to form the chelate. However, under appropriate conditions the coordination number of the magnesium may allow for more than two ligands to be present in the chelate. In those instances the chelate can contain anywhere from one to two ligands each of glycine and glutamine. Further, a ligand consisting of a dipeptide of glycine, glutamine or a glycine-glutamine dipeptide can be used.

When reference is made to either "chelate" or "complex" it is to be noted that these terms are not used interchangeably. On the other hand, although they may be differentiated technically, the terms "complex" and "proteinate" may be interchanged.

"Chromium salt" means an inorganic salt of trivalent chromium such as chromium chloride, and chromium sulfate. "Chromium complex" or "chromium chelate" means an organic complex or chelate of trivalent chromium and can be derived from various forms. Brewers yeast or the GTF factor contained therein can be utilized. GTF factor is thought to be a chromium nicotinate chelate or complex which may or may not involve the use of the amino acids glycine and cysteine. The exact GTF structure is speculative and there are differing opinions, even by the experts, on that matter. A chromium amino acid chelate meeting the above amino acid chelate definition can also be utilized as can chromium picolinate. U.S. Pat. No. 4,954,492 references numerous attempts that have been made to prepare synthetic trace metal complexes which exhibit GTF activity to mimic or enhance the GTF activity found in Brewer's yeast. The only limitation as to the chromium salt, complex or chelate is that of adequate functionality in suppressing cortisol levels. For use in the present invention, chromium amino acid chelates are the preferred form of chromium followed by GTF, chromium picolinates and then inorganic chromium salts.

"Carrier" means any suitable carrier and may be caloric or non-caloric. Inert carriers such as those used as tableting aids or lubricants, e.g. magnesium stearate, carbohydrates (sugar or starch) or proteins may be utilized.

"Protein carrier" or "protein based carrier" means a protein or hydrolyzed protein derived from either animal or plant sources and may also contain other additives such as carbohydrates, flavoring agents, vitamins, minerals, and other additives that do not detract from the anabolic properties of the composition to be administered.

"Effective amount" shall mean the amount of each nutrient that is required to bring about the desired anabolic response and may vary considerably according to the individual, his or her genetic makeup, size, weight and environment. It may be difficult to categorically state that "x" grams, milligrams, micrograms, etc. of any given nutrient is sufficient and may have to be empirically determined. The ranges contained herein are adequate to allow one skilled in the art to determine the formulation to be prepared for any given individual.

The composition described is not designed as a significant source of energy in terms of caloric content. Energy nutrition in a balanced formula between carbohydrates, protein and fats will preferably be consumed to provide caloric intake based on the body weight, in pounds, of the individual multiplied by 20 plus 300 to 500 calories on a daily basis. Additionally, digestive enzymes, metabolic aids, antioxidants, and a balanced amount of vitamins and minerals may be utilized in addition to the composition of this invention. Obviously, an adequate exercise protocol is also a desired, if not an essential, factor.

The following discussion is included for purposes of describing the present invention and illustrating a preferred embodiment thereof and is not intended to be limiting in scope of the specific formulas or compositions disclosed. As previously stated, the present invention comprises a composition for use as a nutritional supplement for purposes of promoting anabolism and sustaining the muscles developed at an optimal balance according to the natural or genetic makeup of the individual. The manner in which the composition provides these specific effects will be discussed in greater detail below.

The anabolic compositions of the present invention include a blend of a chromium salt, organic complex or chelate (collectively referred to as "Chromium SCC") and a magnesium glycyl glutaminate chelate (referred to as "$MgGly_xGln_y$") where x is an integer of 1 to 2 and y is an integer of 1 to 2. It is not necessary that x and y be whole integers as not all reactions of magnesium with amino acids glycine and glutamine will proceed to completion in filling all of the coordination numbers of the magnesium ion with a reaction site of an amino acid. Mg(II) generally has a coordination number of 6 and can accommodate two to three glycine ligands. Glycine is the simplest amino acid and therefore presents less stearic hindrance in the formation of a 3:1 ligand to magnesium ratio than other amino acids. Glutamine, being a longer chain amino acid and having a higher molecular weight than glycine can present greater stearic hindrance in forming chelates. Therefore, some coordination sites of magnesium may contain or be filled by waters of hydration. What is important is that the chelate formed contain a ligand to magnesium mole ratio of at least 2:1 with one mole of glycine and one mole of glutamine being present in the chelate. Most typically, the magnesium glycyl glutaminate chelate may be represented at a ligand to metal ratio of 2:1 according to the following formula:

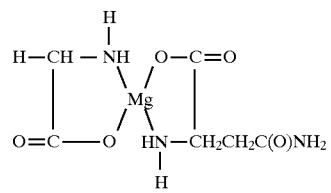

The magnesium content of the magnesium glycyl glutaminate chelate ($MgGly_xGln_y$) will generally range between about 5 to 10% by weight. In a chelate having one glycine ligand and one glutamine ligand the chelate will comprise about 10% magnesium, 60% glutamine ligand and 30% glycine ligand.

Cr(II) and Cr(III) both have coordination numbers of 6 and, by analogy, will form chelates with bidentate ligands at a ligand to chromium ratio of 2:1 to 3:1. Cr(III) is the more active or preferred form of chromium in reducing cortisol levels. The chromium content of chromium chelates and complexes will generally range between about 10 and 20% by weight while the chromium content of chromium salts may range as high as about 35% by weight.

Therefore, in its most fundamental form the composition will contain Chromium SCC and $MgGly_xGln_y$ chelates in the following ranges:

| BASIC INGREDIENTS | RANGES IN PARTS BY WEIGHT | | |
|---|---|---|---|
| | Broad | Preferred | Most Preferred |
| Chromium SCC | $1 \times 1000 \times 10^{-3}$ | $1-200 \times 10^{-3}$ | $20-50 \times 10^{-3}$ |
| MgGly$_x$Gln$_y$ Chelate | 10–10,000 | 10–1,000 | 75–200 |

It is also preferable that the formulation contain one or more additional nutrients selected from the group consisting of a a magnesium amino acid chelate or proteinate (Mg AAC/P), an α-glutaric acid salt of ornithine (α-GAS-Orn), creatine or a salt thereof, and a branched chain amino acid (BCAA) selected from the group consisting of leucine, isoleucine and valine and mixtures thereof. Ranges of these ingredients are:

| ADDITIONAL NUTRIENTS | RANGES IN PARTS BY WEIGHT | | |
|---|---|---|---|
| | Broad | Preferred | Most Preferred |
| Mg AAC/P | 10–10,000 | 10–1,000 | 50–200 |
| α-GAS-Orn | 100–2,000 | 200–1,200 | 300–800 |
| Creatine (or salt) | 1–10,000 | 1–1,000 | 1–100 |
| BCAA | 50–100,000 | 100–10,000 | 1,000–5,000 |

Further to the MgGly$_x$Gln$_y$ Chelate, additional Mg may be supplemented in the form of Mg AAC/P. Since Mg is known to be anabolic, it may be desirable to supplement other bioavailable forms of Mg in amounts comparable to the amount of Mg administered as the MGly$_x$Gln$_y$ Chelate. However, this does not mean that the Mg dosage must be strictly administered as a 1:1 MgGly$_x$Gln$_y$ Chelate:Mg AAC/P ratio as optimal ratios may vary according to the needs of an individual. Hence Mg ratios varying from 10:1 to 1:10 might be considered adequate with ratios of 5:1 to 1:5 being preferred with 1:1 ratios being generally considered optimal.

The α-glutaric acid salt of ornithine (α-GAS-Orn) when present is thought to stimulate the secretion growth hormones and possesses some of the same properties as glutamine in muscle synthesis.

Creatine or a salt thereof is a precursor to phosphocreatine which is a source of high energy storage in muscle.

As referenced above BCAA refers to branched chain amino acids selected from the group consisting of leucine, isoleucine and valine or mixtures thereof. Each BCAA may be present in the stated amounts. Therefore, if all three are present the total BCAA content could be from 150 to 300,000 parts by weight. The BCAA amino acids form about one third of the amino acid pool from which protein is synthesized in the body. These are also absorbed more rapidly than other amino acids. As such, other than glutamine, BCAA's are perhaps the group most highly utilized in muscle synthesis.

The above ingredients have been stated in terms of parts by weight in order to show the relative proportion of one ingredient to another. The "unit dosage" amount of each ingredient may be obtained by converting each part by weight into a milligram in the metric system. In other words, a unit dosage of the MgGly$_x$Gln$_y$ chelate will be in the range of 10 to 10,000 milligrams and a unit dosage of the Chromium SCC will be in the range of the 1 to 1,000 μmg (micrograms) or 1 to 1,000×$10^{-3}$ milligrams.

The concentration of each ingredient will obviously be a function of how many ingredients are in a unit dosage form. It is generally desired that each unit dosage be in the range of between about 5 to 50 grams (5,000 to 50,000 milligrams). Hence, any difference between the sum of the unit dosage weights of the ingredients named above and the overall unit dosage will preferably be made up of a carrier and preferably a protein carrier. In the alternative, if the unit dosage is too great to be administered at one time, it may be apportioned into multiple doses and be administered over a given period of time. A unit dosage may or may not be a daily dosage.

In reference to the unit dosage, the amount of chromium in the Chromium SCC, and magnesium and glutamine in the MgGly$_x$Gln$_y$ chelate are generally sufficient to bring about the desired anabolic response. At a minimum, each unit dosage should contain at least $0.1 \times 10^{-3}$ mg of chromium, 1 mg of magnesium and 6 mgs of glutamine and will preferably contain at least $1 \times 10^{-3}$ mg of chromium, 5 mgs of magnesium and 30 mgs of glutamine. However, as noted above, it may be highly desirable to additionally utilize one or more members selected from the group consisting of Mg AAC/P, α-GAS-Orn and BCAA to optimize an anabolic response in any given individual. If a single unit dosage is not sufficient to provide the desired anabolic response, it may be necessary to modify the daily dosage to include multiple administrations of the unit dosage.

The following examples show oral administration of MgGly$_x$Gln$_y$ Chelate where x and y are each 1 and the effect it has on the glutamine plasma levels and the role it plays in muscle metabolism.

EXAMPLE 1

A mixture was formulated containing 400 mgs of stabilized MgGly$_x$Gln$_y$ Chelate (x and y=1); $100 \times 10^{-3}$ mgs of chromium amino acid chelate (about 20% w. chromium), 200 mg of creatine monohydrate, 2,000 mgs of branched-chain amino acids and 15 mgs each of calcium and magnesium amino acid chelates. This mixture was administered daily to 11 body builders during an eight week study.

To three other groups with four participants each, 2,000 mgs of the anabolic steroid, testosterone, was administered daily instead of the above formulation.

The purpose of the study was to compare the effectiveness of a non-steroid anabolic supplement with anabolic steroids in a muscle mass and body building program.

At the end of the eight week study the participants were examined to determine weight gain as lean body mass. Additionally, blood pressure, total cholesterol, HDL cholesterol and triglycerides contents were monitored.

The participants taking the non-steroidal composition gained an average of 3.2 kg of lean body mass during the 8-week study. One group taking the anabolic steroid gained an average of 3.6 kg of lean body mass and the other two groups averaged 2.7 kg of lean body mass.

No detrimental effects of cardiovascular risk factors as measured by blood pressure, total cholesterol, HDL cholesterol and triglycerides were noted with the group taking the non-steroidal composition.

EXAMPLE 2

A composition containing 400 mgs of stabilized MgGly$_x$Gln$_y$ Chelate (x and y=1) and $100 \times 10_{-3}$ mgs of a chromium amino acid chelate (about 20% chromium) was administered to seven healthy males to determine the effect on plasma glutamine.

The composition was formulated as a powder and was dissolved in a cup of water and consumed immediately after taking a forearm venous blood sample from each subject. Three additional samples of blood were then taken at 30 minute intervals for 90 minutes. Six of the seven subjects responded with an increase in plasma glutamine at 30 minutes and 4 remained at or above the initial sample value at 90 minutes. These findings demonstrate that administering even a small amount of $MgGly_xGln_y$ Chelate, and a chromium supplement is capable of elevating the glutamine plasma level.

The following compositions, suitable for human oral consumption as well as enteral or parental nutrition, have been formulated and are representative of the invention.

EXAMPLE 3

A powder was formulated such that each tablespoon contained 400 mgs of $MgGly_xGln_y$ Chelate (x and y=1), $100 \times 10^{-3}$ mgs of chromium amino acid chelate (about 20% w chromium); 100 mgs of M-500 (a partially hydrolyzed food starch), 2,000 mgs of creatine monohydrate, 1,500 mgs of a branched chain amino acid mixture comprising 500 mg of leucine, 500 mg of valine and 500 mg of isoleucine, 150 mgs of a magnesium amino acid chelate, 50 mg of the α-glutaric acid salt of ornithine, 200 mg of acetyl glutamine, 50 mg of potassium amino acid complex, 15 mg of sodium amino acid complex, and 25 mgs of calcium amino acid chelate.

EXAMPLE 4

$MgGly_xGln_y$ Chelate, and chromium amino acid chelate were formulated as mixtures and filled into gelatin capsules. Each capsule was formulated to contain either 250 or 500 mg of $MgGly_xGln_y$ Chelate (x and y=1), and either $50 \times 10^{-3}$ or $75 \times 10^{-3}$ mg of chromium amino acid chelate (about 20% chromium).

EXAMPLE 5

$MgGly_xGln_y$ Chelate, and chromium amino acid chelate, as used in the above Examples, were combined with lactic acid bacteria, such as lactobacillus acidophilus and lactobacillus bulgaricus, in combination with certain chelated minerals, 10 mg each of zinc, manganese, copper amino acid chelates and filled into gelatin capsules. Each capsule was formulated to contain 100 mg of MGG and $200 \times 10^{-3}$ mg of chromium amino acid chelate.

EXAMPLE 6

A powder was formulated and filled into gelatin capsules such that each capsule contained 300 mgs of $MgGly_xGln_y$ Chelate (x and y=1), $100 \times 10^{-3}$ mgs of chromium amino acid chelate (about 20% w chromium); 100 mgs of creatine monohydrate, 50 mgs of carnitine, and 10 mgs each of calcium and magnesium amino acid chelates.

EXAMPLE 7

A powder was formulated and filled into gelatin capsules such that each capsule contained 400 mgs of $MgGly_xGln_y$ Chelate (x and y=1), $50 \times 10^{-3}$ mgs of chromium amino acid chelate (about 20% w chromium); 200 mgs of creatine monohydrate, and 15 mgs each of calcium and magnesium amino acid chelates.

While the above provides a detailed description of the invention and the best mode of practicing it to the extent that it has been developed, the invention is not to be limited solely to the description and examples. There are modifications which may become apparent to one skilled in the art in view of the description contained herein. Therefore, the invention is to be limited in scope only by the following claims and their functional equivalents.

We claim:

1. An anabolic composition for enteral or parenteral administration comprising:
    (a) $1-1,000 \times 10^{-3}$ parts by weight of a chromium salt, complex or chelate, and
    (b) 10–10,000 parts by weight of a magnesium glycyl glutaminate chelate of the formula $MgGly_xGln_y$ where x is an integer of 1 or 2 and y is an integer of 1 or 2.

2. The anabolic composition of claim 1 in unit dosage form wherein each dosage unit comprises
    (a) $1-1,000 \times 10^{-3}$ milligrams of said chromium salt, complex or chelate, and
    (b) 10–10,000 milligrams of said magnesium glycyl glutaminate chelate.

3. The anabolic composition of claim 2 formulated for enteral administration comprising said unit dosage form contained in one or more capsules.

4. The anabolic composition of claim 2 formulated for enteral administration comprising said unit dosage form admixed in a carrier selected from the group consisting of carbohydrates and proteins and mixtures thereof.

5. The anabolic composition of claim 4 wherein said carrier contains one or more proteins and additionally containing one or more proteolytic enzymes.

6. The anabolic composition of claim 2 wherein x and y are each 1.

7. The anabolic composition of claim 2 wherein said chromium is present as an amino acid chelate.

8. An anabolic composition for enteral or parenteral administration comprising:
    (a) $1-1,000 \times 10^{-3}$ by weight of a chromium salt, complex or chelate, and
    (b) 10–10,000 parts by weight of a magnesium glycyl glutaminate chelate of the formula $MgGly_xGln_y$, where x is an integer of 1 or 2 and y is an integer of 1 or 2, and an effective amount or amounts of at least one additional member selected from the group consisting of:
    (c) a magnesium amino acid chelate or proteinate,
    (d) an α-glutaric acid salt of ornithine,
    (e) creatine or a salt thereof, and
    (f) a branched chain amino acid selected from the group consisting of leucine, isoleucine and valine and mixtures thereof.

9. The anabolic composition of claim 8 wherein said at least one additional member is selected from the group consisting of
    (a) 10–10,000 parts by weight of a magnesium amino acid chelate or proteinate,
    (b) 100–2000 parts by weight of an α-glutaric acid salt of ornithine,
    (c) 1–10,000 parts by weight of creatine or a salt thereof, and
    (d) 50–100,000 parts by weight of a branched chain amino acid selected from the group consisting of leucine, isoleucine and valine and mixtures thereof.

10. The anabolic composition of claim 9 in unit dosage form wherein each dosage unit comprises
    (a) $1-1000 \times 10^{-3}$ milligrams of said chromium salt, complex or chelate, and (b) 10–10,000 milligrams of said magnesium glycyl glutaminate chelate and at least one additional member selected from the group consisting of (c) 10–10,000 milligrams of a magnesium amino acid chelate or proteinate, (d) 100–2000 milligrams of an α-glutaric acid salt of ornithine, (e) 1–10,000 milligrams of creatine or a salt thereof, and (f) 50–100,000 milligrams of a branched chain amino acid selected from the group consisting of leucine, isoleucine and valine and mixtures thereof.

11. The anabolic composition of claim 10 containing a magnesium amino acid chelate or proteinate.

12. The anabolic composition of claim 10 containing an α-glutaric acid salt of ornithine.

13. The anabolic composition of claim 10 containing creatine or a salt thereof.

14. The anabolic composition of claim 10 containing a branched chain amino acid selected from the group consisting of leucine, isoleucine and valine and mixtures thereof.

15. The anabolic composition of claim 10 formulated for enteral administration comprising said unit dosage form contained in one or more capsules.

16. The anabolic composition of claim 10 formulated for enteral administration comprising said unit dosage form admixed in a carrier selected from the group consisting of carbohydrates and proteins and mixtures thereof.

17. The anabolic composition of claim 16 wherein said carrier contains one or more proteins and additionally containing one or more proteolytic enzymes.

18. The anabolic composition of claim 10 wherein x and y are each 1.

19. The anabolic composition of claim 10 wherein said chromium is present as an amino acid chelate.

20. A method for the building and sustaining of muscle mass in a human or other warm-blooded animal subject which comprises administering to said subject an anabolic composition comprising:

(a) $1-1,000 \times 10^{-3}$ parts by weight of a chromium salt, complex or chelate, and (b) 10–10,000 parts by weight of a magnesium glycyl glutaminate chelate of the formula $MgGly_xGln_y$ where x is an integer of 1 or 2 and y is an integer of 1 or 2.

21. The method of claim 20 administered in unit dosage form wherein each dosage unit comprises (a) $1-1,000 \times 10_{-3}$ milligrams of said chromium salt, complex or chelate, and (b) 10–10,000 milligrams of said magnesium glycyl glutaminate chelate.

22. The method of claim 21 administered enterally wherein said unit dosage form is contained in one or more capsules.

23. The method of claim 21 administered enterally wherein said unit dosage form is admixed in a carrier selected from the group consisting of carbohydrates and proteins and mixtures thereof.

24. The method of claim 23 wherein said carrier contains one or more proteins and additionally containing one or more proteolytic enzymes.

25. The method of claim 21 wherein x and y are each 1.

26. The method of claim 21 wherein said chromium is present as an amino acid chelate.

27. A method for the building and sustaining of muscle mass in a human or other warm blooded animal subject which comprises administering to said subject an anabolic composition comprising:

(a) $1-1,000 \times 10^{-3}$ parts by weight of a chromium salt, complex or chelate, and (b) 10–10,000 parts by weight of a magnesium glycyl glutaminate chelate of the formula $MgGly_xGln_y$ where x is an integer of 1 or 2 and y is an integer of 1 or 2, and an effective amount or amounts of at least one additional member selected from the group consisting of (c) a magnesium amino acid chelate or proteinate, (d) an α-glutaric acid salt of ornithine, (e) creatine or a salt thereof, and (f) a branched chain amino acid selected from the group consisting of leucine, isoleucine and valine and mixtures thereof.

28. The method of claim 27 wherein said composition wherein said at least one additional member is selected from the group consisting of (a) 10–10,000 parts by weight of a magnesium amino acid chelate or proteinate, (b) 100–2000 parts by weight of an α-glutaric acid salt of ornithine, (c) 1–10,000 parts by weight of creatine or a salt thereof, and (d) 50–100,000 parts by weight of a branched chain amino acid selected from the group consisting of leucine, isoleucine and valine and mixtures thereof.

29. The method of claim 28 administered in unit dosage form wherein each dosage unit comprises (a) $1-1,000 \times 10^{-3}$ milligrams of said chromium salt, complex or chelate, and (b) 10–10,000 milligrams of said magnesium glycyl glutaminate chelate and at least one additional member selected from the group consisting of (c) 10–10,000 milligrams of a magnesium amino acid chelate or proteinate, (d) 100–2000 milligrams of an α-glutaric acid salt of ornithine, (e) 1–10,000 milligrams of creatine or a salt thereof, and (f) 50–100,000 milligrams of a branched chain amino acid selected from the group consisting of leucine, isoleucine and valine and mixtures thereof.

30. The method of claim 29 wherein said unit dosage form contains a magnesium amino acid chelate or proteinate.

31. The method of claim 29 wherein said unit dosage form contains an α-glutaric acid salt of ornithine.

32. The method of claim 29 wherein said unit dosage form comprises creatine or a salt thereof.

33. The method of claim 29 wherein said unit dosage form comprises a branched chain amino acid selected from the group consisting of leucine, isoleucine and valine and mixtures thereof.

34. The method of claim 29 administered enterally wherein said unit dosage form is in one or more capsules.

35. The method of claim 29 administered enterally wherein said unit dosage form is admixed in a carrier selected from the group consisting of carbohydrates and proteins and mixtures thereof.

36. The method of claim 35 wherein said carrier contains one or more proteins and additionally containing one or more proteolytic enzymes.

37. The method of claim 29 wherein x and y are each 1.

38. The method of claim 29 wherein said chromium is present as an amino acid chelate.

* * * * *